(12) United States Patent
Honjo et al.

(10) Patent No.: US 7,407,767 B2
(45) Date of Patent: Aug. 5, 2008

(54) METHOD OF SCREENING REMEDY FOR HEART DISEASE AND MEDICINAL COMPOSITION FOR TREATING HEART DISEASE

(75) Inventors: Tasuku Honjo, 19-4, Ohsagi-cho, Iwakura, Sakyo-ku, Kyoto (JP) 606-0001; Taku Okazaki, Kyoto (JP)

(73) Assignees: Ono Pharmaceutical Co., Ltd., Okaka (JP); Tasuku Honjo, Kyoto (JP)

( * ) Notice: Subject to any disclaimer, the term of this patent is extended or adjusted under 35 U.S.C. 154(b) by 0 days.

(21) Appl. No.: 10/553,406

(22) PCT Filed: Apr. 15, 2004

(86) PCT No.: PCT/JP2004/005382

§ 371 (c)(1), (2), (4) Date: Oct. 17, 2005

(87) PCT Pub. No.: WO2004/091476

PCT Pub. Date: Oct. 28, 2004

(65) Prior Publication Data

US 2006/0246525 A1 Nov. 2, 2006

(30) Foreign Application Priority Data

Apr. 16, 2003 (JP) ............................. 2003-111703

(51) Int. Cl.
*G01N 33/53* (2006.01)
(52) U.S. Cl. ...................................... 435/7.2
(58) Field of Classification Search ..................... 435/4, 435/7.1, 287.1–287.2, 7.2; 422/67, 167
See application file for complete search history.

(56) References Cited

U.S. PATENT DOCUMENTS

| | | | | |
|---|---|---|---|---|
| 4,637,880 A | * | 1/1987 | Halbert | 210/638 |
| 5,534,615 A | * | 7/1996 | Baker et al. | 530/350 |
| 5,795,725 A | * | 8/1998 | Buechler et al. | 435/7.1 |
| 7,064,180 B2 | * | 6/2006 | Arnaout et al. | 530/324 |
| 7,064,189 B2 | * | 6/2006 | Salcedo et al. | 530/388.85 |

| | | |
|---|---|---|
| 2002/0127602 A1 | 9/2002 | Shi et al. |

FOREIGN PATENT DOCUMENTS

| | | |
|---|---|---|
| JP | 9-503050 A | 3/1997 |
| WO | WO 94/27156 A1 | 11/1994 |
| WO | WO 96/10076 A1 | 4/1996 |
| WO | WO 96/22535 A1 | 7/1996 |
| WO | WO 00/54770 A1 | 9/2000 |
| WO | WO 02/39813 A1 | 5/2002 |
| WO | WO 03/006950 A2 | 1/2003 |

OTHER PUBLICATIONS

XP-000647600—G. Wallukat et al., "Removal of autoantibodies in dilated cardiomyopathy by immunoadsorption" (1996), International Journal of Cardiology, vol. 54, No. 2, pp. 191-195.
XP-002376772—Taku Okazaki et al., "Autoantibodies against cardiac troponin I are responsible for dilated cardiomyopathy in PD-1-deficient mice" (2003), Nature Medicine, vol. 9, No. 12, pp. 1477-1483.
XP-002376773—Alida L.P. et al., "Circulating cardiac autoantibodies in dilated cardiomyopathy and myocarditis: pathogenetic and clinical significance" (2002), The European Journal of Heart Failure, vol. 4, No. 4, pp. 411-417.
XP-002377071—Hiroyuki Nishimura et al., "Autoimmune Dilated Cardiomyopathy in PD-1 Receptor-Deficient Mice" (2001), Science, vol. 291, No. 5502, pp. 319-322.
Partial European Search Report dated May 12, 2006.

* cited by examiner

*Primary Examiner*—Ann Y Lam
(74) *Attorney, Agent, or Firm*—Sughrue Mion, PLLC

(57) ABSTRACT

A method for screening a substance that inhibits the onset of anti-cardiac troponin I autoantibody-related disease, a pharmaceutical composition and a base material for therapy of cardiac disease that contains the substance obtained by aforesaid method thereof, a therapeutic apparatus that removes anti-troponin I autoantibody for aforesaid antibody related disease, a method of making an animal model for evaluating cardiac disease characterized by administrating anti-cardiac troponin I antibody, a method of selection of a therapeutic substance for cardiac disease characterized by using aforesaid animals, and a diagnosis of dilated cardiomyopathy characterized by measuring anti-cardiac troponin I autoantibody. An apparatus of the present invention that removes anti-cardiac troponin I antibody and a pharmaceutical composition for therapy of the antibody related disease may be useful for a therapy and/or prevention of cardiac disease.

2 Claims, 5 Drawing Sheets

FIG. 5

|  | Control IgG | Anti-myocardiac troponin I | statistically significant difference |
|---|---|---|---|
| Body weight (g) | 23.2±0.9 | 22.3±0.4 | N.S. |
| Heart weight (g) | 131.7±6.0 | 130.7±4.3 | N.S. |
| Heart rate (min$^{-1}$) | 370±4 | 369±10 | N.S. |
| ESP (mmHg) | 103.8±6.7 | 98.1±4.2 | N.S. |
| EDP (mmHg) | 2.3±0.4 | 8.4±2.0 | <0.05 |
| SVI (μl/g) | 0.66±0.04 | 0.57±0.10 | N.S. |
| CI (μl/min/g) | 242±15 | 210±35 | N.S. |
| RA$_{mean}$ (mmHg) | 2.9±0.3 | 4.3±0.7 | N.S. |
| SVRI (mmHg/mg·min·g) | 315.6±16.5 | 387.5±81.1 | <0.05 |
| Systolic function | | | |
| dP/dt$_{max}$ (mmHg/s) | 8295±762 | 5463±649 | <0.05 |
| NL $E_{es}$ (mmHg/μl·100mg) | 17.36±4.63 | 5.27±0.82 | <0.05 |
| $E_a/E_{es}$ | 0.70±0.19 | 2.01±0.32 | <0.05 |
| Diastolic function | | | |
| dP/dt$_{min}$ (mmHg/s) | -5171±218 | -3413±531 | <0.05 |
| (dP/dt$_{max}$)/(dP/dt$_{min}$) | 1.60±0.13 | 1.67±0.13 | N.S. |
| NL $E_{ed}$ (mmHg/μl·100mg) | 0.33±0.45 | 0.49±0.46 | N.S. |
| τ (ms) | 101±1.1 | 11.7±2.6 | N.S. |

ESP, end-systolic pressure; EDP, end-diastlic pressure; SVI, strole-volume index; SVRI, systemic vascular resistance index; CI, cardiac index; RA$_{mean}$, mean right atrial pressure; NL $E_{es}$, normalized end-systolic volume elastance; NL $E_{ed}$, normalized end-diatolic volume elastance; τ, monoexponential time constant of relaxation.

METHOD OF SCREENING REMEDY FOR HEART DISEASE AND MEDICINAL COMPOSITION FOR TREATING HEART DISEASE

TECHNICAL FIELD

The present invention relates to; a screening method of a substance that inhibits the onset of anti-troponin I autoantibody-related disease; a pharmaceutical composition or a base material for therapy of cardiac disease including a substance obtained by the above method; a therapeutic apparatus that removes anti-troponin I autoantibodies for aforesaid antibody related disease; a method of making an animal model for evaluating cardiac disease characterized by administrating anti-cardiac troponin I antibodies; a method of screening a substance for therapy of cardiac disease characterized by using the animal; and a diagnosis of dilated cardiomyopathy characterized by measuring the amount of anti-cardiac troponin I autoantibodies.

BACKGROUND ART

Dilated cardiomyopathy is one of the myocardial diseases characterized by progressive depression of myocardial contractile function and dilated ventricle, and the dysfunction of depressing dilated left ventricle is present. This disease often develops chronically and the prognosis is poor in the majority of cases. Therefore, in Europe and the United States, cardiac transplantation is necessary for this disease in many cases, and above 90% of cardiac transplantation cases in Japan were those of patients with this disease. 30% of dilated cardiomyopathy patients are said to have a congenital mutation in the gene that codes an important component of myocardium, which links cytoskeleton to cell matrix. However, the causes of the rest of cases are unknown. In both cases, the onset rate is very high (36.5 in 100,000 people) and the death rate is also high. However, there is no effective therapy except for cardiac transplantation.

In addition to ischemic, toxic, metabolic, infectious, and genetic causes, autoimmunity has been suspected to be one of the main causes. Several papers have reported that the patients of myocarditis or cryptogenic dilated cardiomyopathy have heart reactive autoantibodies. Antibodies to the mitochondrial ADP/ATP translocator or β1-adrenoceptor, which are often found in human patients, have been shown to enhance $Ca^{2+}$ current (*Journal of Experimental Medicine*, 1988, 168(6), p 2105-2019, *European Journal of Pharmacology*, 2001, 423(2-3), p 115-119). In addition, immunoabsorption has been reported to have beneficial effects. (*Circulation*, 2001, 103(22), p 2681-2686). Stephan B. Felix proved that the therapy with immunoabsorption made patients' hemodynamics improved and the column eluent, which contains harvested antibodies from immunoabsorption column, decreased cell contraction in myocardial cells because of calcium current suppression (*Journal of the American College of Cardiology*, 2002, 39(4), p 646-652). Experimental studies in rodents have shown that cardiotropic viral infections or immunization with cardiac antigens can elicit injury of cardiomyocytes, leading to cardiomyopathy with concomitant production of heart-reactive autoantibodies and cytotoxic T cells (*Circulation*, 1982, 65(6), p 1230-1235, *Clinical Immunology and Immunopathology*, 1987, 43, 1, p 129-139, *Journal of Molecular and Cellular Cardiology*, 1997, 29(2), p 641-655, Journal of Immunology, 1987, 139 (11), p 3630-3636). However, because autoimmune responses observed in the rodent models and human patients could be secondary to heart inflammation, the involvement of autoimmunity in the pathogenesis of dilated cardiomyopathy is still debatable (*Journal of Immunology*, 1990, 145(12), p 4094-4100).

PD-1 is an immune inhibitory receptor belonging to CD28/CTLA-4 family and inhibits antigen receptor-mediated signaling by recruiting SHP-2 upon engagement with its ligands, PD-L1 or PD-L2 (*Current Opinion Immunology*, 2002, 14(6), p 779-782). C57BL/B6 PD-1-deficient mice developed lupus-like glomerulonephritis and arthritis (*Current Opinion Immunology*, 2002, 14(6), p 779-782). The inventors have recently shown that BALB/c PD-1-deficient mice develop dilated cardiomyopathy (*Science*, 2001, 291(5502), p 319-322, WO02/39813).

The dilated heart of the mice showed prominent depositions of immune complex on myocardial cells. Furthermore, sera from PD-1-deficient mice contained high-titer autoantibodies against a heart-specific, 30-kDa protein. Although these results support the hypothesis that autoimmunity is a probable cause of dilated cardiomyopathy, there was no direct evidence. Therefore, it is essential to identify the 30-kDa antigen and assess the pathogenic role of the antigen-specific autoimmune reaction in dilated cardiomyopathy.

DISCLOSURE OF THE INVENTION

The task of the present invention is the provision of a pharmaceutical composition and a therapeutic apparatus for anti-cardiac troponin I autoantibody-related disease, and a diagnosis thereof.

The inventors of the present invention showed that anti-cardiac troponin I autoantibodies existed in serum of PD-1-deficient mouse, and identified that autoantibodies against cardiac troponin I were the onset factor of dilated cardiomyopathy.

The inventors of the present invention thought that the anti-cardiac troponin I autoantibodies were involved in the onset of dilated cardiomyopathy in PD-1-deficient mouse because of the existence of anti-cardiac troponin I autoantibody in serum of PD-1-deficient mouse and the result of the analysis in the depositions of immune complex on the surface of myocardial cells and the like. Concretely, binding of anti-cardiac troponin I autoantibody to cardiac troponin I resulted in compromising cardiac function. Moreover, we showed that voltage-dependent calcium current in normal myocardial cells was increased by addition of monoclonal anti-cardiac troponin I autoantibodies suggesting that cardiac troponin I expressed on myocardial cells has a role in controlling calcium current. From above results and discussion, the inventors of the present invention concluded that the anti-cardiac troponin I caused dilated cardiomyopathy by chronic rise in calcium current of myocardial cells. Therefore, the anti-cardiac troponin I autoantibody-related disease are thought to be treatable by a removal of anti-cardiac troponin I autoantibodies, an inhibition of interaction between anti-cardiac troponin I autoantibody and cardiac troponin I, an inhibition of effect of anti-cardiac troponin I autoantibody to its target tissues, and an inhibition of anti-cardiac troponin I autoantibody production. The diagnosis of the anti-cardiac troponin I autoantibody-related disease may be carried out by measuring the amount of antibody in collected blood, sera, blood plasma, urine and tissue of the patients.

Based on above finding and discussion, the inventors completed the invention related to the following; a screening method of a substance that inhibits the onset of anti-cardiac troponin I autoantibody-related diseases, a pharmaceutical composition and a base material for therapy of cardiac disease that contains a substance obtained by the above method, a therapeutic apparatus for anti-cardiac troponin I autoantibody-related diseases by removing the antibody, a method of making animal model for evaluating cardiac disease, characterized by administration of anti-cardiac troponin I autoantibody, a method of selection of a therapeutic substance for cardiac disease characterized by use of the above animal and diagnostic method of dilated cardiomyopathy.

The present invention relates to the followings:

1. A screening method of a substance that inhibits interaction between anti-troponin I antibody and cardiac troponin I, which comprises measuring and evaluating the inhibitory activity of a test substance on interaction between anti-cardiac troponin I antibody and cardiac troponin I after contacting the anti-cardiac troponin I antibody, the cardiac troponin I and the test substance.
2. A screening method of a substance that inhibits the effect of anti-troponin I to a target tissue, which comprises measuring and evaluating the inhibitory activity of a test substance on the effect of anti-cardiac troponin I antibody on a target tissue after contacting the anti-cardiac troponin I, the target tissue and the test substance.
3. The screening method according to the above 2, wherein the target tissue is a myocardial cell.
4. A pharmaceutical composition of therapy for cardiac disease which is made by steps comprising a step of selecting a substance with activity by the screening method according to any one of the above 1 to 3, a step of manufacturing the above selected substance, and a step of mixing the substance manufactured by the above described step with a pharmaceutically acceptable solvent for formulation.
5. A pharmaceutical composition of therapy for cardiac disease, which comprises at least one selected from cardiac troponin I protein, a partial protein thereof, and a modified protein thereof as an active ingredient.
6. The pharmaceutical composition of therapy for cardiac disease according to the above 4 or 5, wherein the cardiac disease is dilated cardiomyopathy.
7. A therapeutic base material for cardiac disease coupled with a substance selected by the method according to any one of the above 1 to 3.
8. A therapeutic base material for cardiac disease coupled with at least one selected from cardiac troponin I, its partial protein, and a modified protein thereof
9. The therapeutic base material for cardiac disease according to the above 7 or 8, wherein the cardiac disease is dilated cardiomyopathy.
10. An apparatus for therapy of cardiac disease, which comprises a plasma separating apparatus; an extracorporeal immunity absorbing apparatus that contacts between separated plasma and the therapeutic base material for cardiac disease described in the above 7 and 8; and a reflux apparatus which mixes plasma treated with the above described extracorporeal immunity absorbing apparatus into separated hemocytes, and send it back into body again.
11. The apparatus for therapy of cardiac disease according to the above 10, wherein the cardiac disease is a dilated cardiomyopathy.
12. A method for making an animal model for evaluating cardiac disease, which comprises administering the anti-cardiac troponin I antibody.
13. The method for making an animal model for evaluation of cardiac disease according to the above 12, wherein the cardiac disease is dilated cardiomyopathy.
14. A method of screening a substance for therapy of cardiac disease, which comprises determining the effect of a test substance to cardiac disease after administration of the substance to an animal made by the method according to the above 12.
15. A method of screening a substance for therapy of dilated cardiomyopathy, which comprises determining the effect of a test substance to cardiac disease after administration of the substance to an animal made by the method according to the above 13.
16. A pharmaceutical composition for therapy of dilated cardiomyopathy, which comprises a substance that inhibits the production of anti-cardiac troponin I autoantibody as an active ingredient.
17. A diagnosis method of dilated cardiomyopathy, which comprises measuring an amount of anti-cardiac troponin I autoantibody.

In the present invention, cardiac troponin I protein includes cardiac troponin I of mammal, such as mouse, rat, hamster, guinea pig, dog, pig, monkey and human.

Human cardiac troponin I protein includes the 210-aa protein that has the sequence indicated protein ID: CAA38102.1 or a mutant protein that has at least one or more than two amino acid substitution thereof. Moreover, human cardiac troponin I protein and its mutant protein include the protein that has at least 70%, homology, preferably 80 or 90% homology, more preferably 95% homology in the consecutive amino acid region of which length is at least 10 aa, preferably at least 30, 40, 50, 60, 100, or 200 aa.

A partial protein of cardiac troponin I includes the partial protein of cardiac troponin I protein and its mutant protein. These partial proteins can bind the anti-cardiac troponin I autoantibody and contain at least continuous 10 aa, preferably at least continuous 30, 40, 50, 60, 100 or 200 aa of normal or mutational cardiac troponin I. Moreover, in case of human, more preferably the partial protein has the region including less than 30% sequence homology to slow skeletal muscle type troponin I (RefSeq data sources; protein ID: NP_003281), and quick skeletal muscle type troponin I (RefSeq data sources; protein ID: BC032148). Furthermore, partial protein of cardiac troponin I may be fused with another protein.

In the present invention, anti-cardiac troponin I antibodies include any antibodies which can specifically bind to cardiac troponin I and partial protein thereof and anti-cardiac troponin I autoantibody. Polyclonal or monoclonal antibodies of the present antibody may be obtained from immunized rodents by using a general method (Kohler, Milstein, *Nature*, 1975, 256, p 495-497). The antibodies and its partial fragment are any antibodies such as polyclonal antibodies, monoclonal antibodies, and partially or fully humanized antibodies and its shortened type (such as F(ab')2, Fab', Fab, or F(v)). Fragments of F(ab')2, Fab', Fab, or F(v) antibody can be obtained by cleavages of complete antibody with proteases, if necessary additively with reduction. By isolating cDNA from the antibody-producing hybridoma, and using the expression vector made by genetic modification, the antibody, its fragment and the fused protein of the antibody fragment with another protein can be obtained.

An anti-cardiac troponin I autoantibody means the antibody that is produced by autoimmunocyte and that reacts with autologous cardiac troponin I protein. Autoantibodies can be comprised of any subtype of the immunoglobulin. An anti-cardiac troponin I antibody may be obtained in the form contained in circulated blood, collected blood, sera, blood plasma, urine and tissue or substantial pure state purified therefrom. The autoanitibody may be obtained by isolating or purifying from the objective patients' blood. Furthermore, anti-cardiac troponin I autoantibody and segment thereof or fusion protein between segment thereof and another protein may be produced by using genetically modified expression vector. The vector may be obtained by using isolated autoantibody cDNA from substantial single lymphocyte of objective patients which produces anti-cardiac troponin I autoantibody.

In the present invention, the target tissue includes a part of the tissue such as heart, atrium, ventricle, valve, heart wall, inferior vena cava, superior vena cava, aorta, pulmonary trunk, left superior pulmonary vein, coronary artery, and coronary vein and primary cultured cell and cell line derived from the above tissues. Preferably, cardiomyocytes and the tissue expressing cardiac troponin I or tissue-derived cells which express cardiac troponin I.

In the present invention, test substance is selected from peptide, polypeptide, nucleotide, polynucleotide, polysaccharide, natural product, fermentation product, cell extract, plant extract, animal tissue extract, antibody, antiserum, derivatives thereof, modified substance thereof, synthesized compound, organic synthesized compound and the like.

A substance that inhibits the effect of autoantibodies on the target tissue may be every substance that inhibits the effect of autoantibodies exerted by binding to the tissue which expresses or contains their antigens, preferably antigenic protein, a partial protein thereof, and modified protein thereof, more preferably the base material coupled with antigenic protein, a partial protein thereof and modified protein thereof.

A substance that inhibits interaction between anti-cardiac troponin I antibody and cardiac troponin I may be every substance that inhibits the binding of cardiac troponin I to cardiac troponin I antibody. One example is a substance that binds to a part responsible for antigen recognition. Preferable substance is such as cardiac troponin I protein, a portion thereof and modified protein thereof, and more preferable is the base material coupled with cardiac troponin I protein, a partial protein thereof and modified protein thereof.

A substance of the present invention that inhibits the effect of anti-cardiac troponin I to the target tissue may be every substance that inhibits binding of antibody to the target tissue, the enhancement or suppression of electrophysiological signal that occurs by the effect of the antibody, and tissue damage by the effect of the antibody. One example is a substance that binds to antigen-recognition site of the antibody. Cardiac troponin I or its partial protein, or modified protein thereof is preferable. A base material coupled with cardiac troponin I or its partial protein or modified protein thereof is more preferable.

A screening method of the substance that inhibits interaction between anti-cardiac troponin I antibody and cardiac troponin I, may be done in the way to evaluate interaction between anti-cardiac troponin I antibody and cardiac troponin I qualitatively and quantitatively. The screening may be carried out by such as radioimmunoassay (RIA), chemiluminescent immunoassay (CIA), enzyme immunoassay (EIA), Western blotting, or Biacore. An objective substance can be selected by calculation of the strength of the interaction between anti-cardiac troponin I antibody and cardiac troponin I under existence of control or test substance.

A screening of the substance that inhibits the effect of anti-cardiac troponin I antibody on the target tissue can be carried out by evaluating the effect to target tissue qualitatively and quantitatively. In case that target tissue is a certain type of cells, it can be carried out by the measurement of viable cells (such as MTT assay, XTT assay and FACS), of activity in cell proliferation, of cell activity (such as ATP synthesis activity), of cell damage activity (such as LDH release activity) and the like. In case that cardiomyocyte is chosen for experimental substance, it can be carried out by evaluating the effect of test substance on the increase of $Ca^{2+}$ influx current under existence or non-existence of anti-cardiac troponin I antibodies. In every method, an objective substance can be selected by the comparison of $Ca^{2+}$ influx current between when control substance is added into the cell expressing cardiac troponin I together with anti-cardiac troponin I and when test substance is added into the cell expressing cardiac troponin I together with anti-cardiac troponin I. In case that the target tissue is raw, tissue injury can be evaluated by staining or immunostaining.

The substance selected by the screening for a substance that inhibits interaction between anti-cardiac troponin I antibody and cardiac troponin I or that inhibits the effect of anti-cardiac troponin I on the target tissue may be produced or synthesize substantially in a pure form as a selected peptide, polypeptide, nucleotide, polynucleotide, polysaccharide, natural product, fermentation product, cell extract, plant extract, animal tissue extract, antibody, antiserum, derivatives thereof, modified substance thereof, synthesized compound, organically synthesized compound and the like, by using arbitrary method.

In case that the selected substance is peptide or polypeptide, preferably cardiac troponin I or its partial protein, or modified protein thereof, they may be produced by a protein expression system (host-vector system) with transgenic technology, such as bacteria-, yeast-, insect cell-, mammalian cell-expression system.

A vector may include *Escherichia coli* plasmid (such as pBR322, pBR325, pUC12, pUC13), *Saccharomyces cerevisiae* plasmid (such as pSH19, pSH15), bacteriophage such as λ phage, animal virus (such as retrovirus, vaccinia virus, baculovirus), pA1-11, pXT1, pRc/CMV, pRc/RSV, pcDNAI/Neo and the like. A promoter used in the present invention is any one of promoters that are both adequate to express gene and suitable for host. For example, in case that animal cell is used as host, SRα promoter, SV40 promoter, LTR promoter, CMV promoter and HSV promoter may be used. Among these, CMV (cytomegalovirus) promoter and SRα promoter are preferable. In case that host is insect cell, polyhedrin promoter and P10 promoter are preferable as promoter.

The objective peptide may be obtained by *Escherichia* genera which is transformed with an expression vector and cultured in an adequate medium. If bacteria's signal peptide (such as pelB signal peptide) may be used, the objective peptide may be secreted in its periplasm. Furthermore, a fusion protein of the peptide with the other peptide may be produced.

In case that the objective protein may be expressed in mammalian cell, for example, to secrete the objective peptide in the culture medium, adequate host mammalian cell may be transformed with an adequate expression vector which contained cDNA coding the objective protein, and then the transformant is cultured in an adequate medium.

A host may include, such as *Escherichia* species, *Bacillus* species, yeast cell, insect cell, insect, animal cell, and the like. Examples of *Escherichia* species include *Escherichia coli* K12, DH1, JM103, HB101, JM109, DH5, DH5α and the like. In case that virus is AcNPV, cell line derived from larval of *Spodoptera frugiperda* (Sf cell) may be chosen as a host. In case that virus is BmNPV, such as cell line derived from silkworm larva (BmN cell) may be chosen as a host. Sf cell includes Sf9 cell (ATCC CRL1711), Sf21 (Vaughn, J. L., *In Vivo*, 1977, Vol. 13, p 213-217). Insect includes a larva of silkworm (*Bombyx mori* larva). Animal cell includes, monkey-derived COS-7 cell line, Vero cell line, Chinese hamster ovary cell line (hereinafter referred to as CHO cell), dhfr gene-deficient Chinese hamster cell line (hereinafter referred to as CHO (dhfr-) cell), mouse L cell, mouse AtT-20, mouse myeloma cell, rat GH3, human FL, HEK 293 cell, etc.

Transformation of *Escherichia* species can be carried out in accordance with methods as disclosed in *Proceedings of the National Academy of Sciences of the United State of America*, Vol. 69, 2110 (1972), *Gene*, Vol. 17, 107 (1982) and the like. Transformation of yeast cell can be carried out in accordance with methods as disclosed in *Methods in Enzymology*, 194, 182-187 (1991) and the like. Transformation of insect cells or insects can be carried out in accordance with methods as disclosed in *Bio/Technology*, 6, 47-55, (1988) and the like. Transformation of *Bacillus* species can be carried out in accordance with methods as disclosed in *Molecular & General Genetics*, Vol. 168, 111 (1979) and the like. Transformation of animal cells can be carried out by methods as disclosed in *Cell Engineering*, separate vol. 8, *New Cell Engineering Experiment Protocol*, 263-267 (1995) (Shujun Company), *Virology*, Vol. 52, 456 (1973) and the like.

Cardiac troponin I and partial protein thereof may be produced as a fusion protein with a portion of the other protein. Suitable partial proteins for fusion include histidine tag, Fc fragment of immunoglobulin constant region, GST (glutathione S-transferase) and the like. These can be beneficial to purification steps after mass production, can increase the solubility of fusion protein, and can be expected to increase the conformational stability.

A modified protein includes enzymatically or chemically aminated, phosphorylated, acylated, methylated, esterificated, myristylated, disulfidated, ubqutinated, sugar-residues added, oligosaccharide-added, polysaccharide-added, oxidated, reduced, or hydrolyzed protein at the specific or arbitrary site of the protein.

A protein obtained the above method may be purified in a general method, for example, ion exchange chromatography, gel filtration, hydrophobic chromatography, affinity chromatography (such as, $Ni^{2+}$ ion column, anti-GST antibody affinity column, Protein A affinity column).

A base material coupled with a substance that inhibits the interaction between anti-cardiac troponin I antibody and cardiac troponin I or the effect of the anti-cardiac troponin I antibody on target tissue is a material binding the substance electrostatically, chemically, or biochemically. Among the source of the material, insoluble carrier includes a synthetic polymer (such as polystyrene, polypropylene, polyamide, polyimide, polyaromatic vinyl compound, polyester, polymethyl methacrylate, polysulfone, polyethylene, polyvinyl alcohol, and polytetrafluoroethylene), a natural polymer (such as cellulose, agarose, sepharose, dextran, chitin, chitosan) and a derivative thereof. In addition, it also includes metals, silica gels, diatomaceous earth, celite, zeolite, porous glasses, ionic exchange resin and a derivative thereof, organic or inorganic porous material, magnetic bead, micro bead and the like. The source of the material may not be limited to the above described.

A form of base material in the present invention includes particle, fiber, membrane, hollow fiber and the like. A base material form of the present invention is not limited, but particle or fiber is preferable because of handling convenience. In case of particulate material, particle size is 10-5000 μm in usual, preferably 50-1000 μm at the point of the clogging in filling up a column and the absorption rate of adsorbates, but it is not limited to the above described. Furthermore, adsorbates can be sterilized by auto clave sterilization, EOG sterilization, γ-ray irradiating sterilization and the like.

A binding of the substance to the base material can be carried out by amine coupling, coupling by the use of biotin-avidin interaction, thiolate method, amino-coupling method by the use of carboxyl group, cyanogen bromide method and the like.

An animal model for evaluation of cardiac disease, made by administration of the anti-cardiac troponin I antibody is a mammal that develops cardiac disease like symptom due to damage to cardiac function or tissue by administration anti-cardiac troponin I antibody once or intermittently more than twice. The preferable animal is mouse, rat, hamster, guinea pig, dog, pig, and monkey.

A method for selection of a therapeutic base material for cardiac disease by the administration of test substance to the animal affected with cardiac disease due to administration of the anti-cardiac troponin I antibody is to evaluate improvement of cardiac dysfunction, histological or morphological damage due to administration of the anti-cardiac troponin I antibody. In case that cardiac disease is equivalent of human dilated cardiomyopathy, end-systolic volume, end-diastolic volume, ejection fraction, pressure driving rate, ventricular end-systolic volume elastance, systemic peripheral vascular resistance index, end-diastolic pressure, right-atrial pressure and the like may be evaluated. Cardiac tissue damage also may be evaluated by tissue stain or immunological tissue stain. Test substance mixed with pharmacologically allowable solvent may be administrated orally or parenterally, before, during, or after administration of the anti-cardiac troponin I antibody.

A therapy of anti-cardiac troponin I autoantibody-related diseases may be treated by removing anti-cardiac troponin I autoantibody from a patient's blood and administration of pharmaceutical component for therapy with substance that inhibits the effect of cardiac troponin I autoantibody on target tissue or cell, or the production of anti-cardiac troponin I antibody.

Anti-cardiac troponin I autoantibody-related diseases include cardiac disease, especially dilated cardiomyopathy.

The method of removing anti-cardiac troponin I autoantibody from a patient's blood may be performed by the method consisted the following step; (1) the separation of a patient's blood into hemocyte and plasma, (2) the contact between separated plasma and a base material coupled with a substance that inhibits the interaction between anti-cardiac troponin I antibody and cardiac troponin I, and (3) sending both the mixture of treated plasma in step (2) and separated hemocyte back again into the patient body.

A therapeutic apparatus that removes the anti-cardiac troponin I autoantibody from a patient's blood is a therapeutic apparatus for cardiac disease, preferably for dilated cardiomyopathy containing the following as essential components; (1) an apparatus for plasma separation of collected blood from a patient into plasma and hemocyte, (2) an apparatus for extracorporeal immunity absorption that contacts between separated plasma and therapeutic base material coupled with a substance that inhibits the interaction between anti-cardiac troponin I antibody and cardiac troponin I, and (3) reflux apparatus for sending the treated plasma in step (2) back after mixing with separated hemocyte.

A pharmaceutical composition for therapy of dilated cardiomyopathy containing a substance that inhibits the production of anti-cardiac troponin I autoantibody as an effective component contains a substance that inhibits the production of anti-cardiac troponin I autoantibody. A substance that inhibits the production anti-troponin I autoantibody, is any substance chosen from, for example, a substance that directly or indirectly inhibits the antibody production itself or the extracellular secretion of the antibody, a substance that inhibits any of the differentiation, maturation or proliferation of the clonal lymphocytes producing autoantibody, or a substance that induces apoptosis of the lymphocytes or injures specifically the lymphocyte. In addition, a substance that inhibits the production anti-troponin I autoantibody is also chosen as an immunosuppressive agent that inhibits the entire immunoreactions that is related to the onset of the said disease.

In the present invention, the measurement of cardiac troponin I autoantibody may be carried out by radioimmunoassay (RIA), chemiluminescence immunoassay (CIA), enzyme immunoassay, western blotting, Biacore measurement, and the like. These methods for measurement may be consist of at least (1) contacting and then reacting block for measurement which is electrostatically, chemically or biochemically bound by cardiac troponin I or partial protein thereof with objective sample, such as blood, serum, blood plasma, urine or tissue extract, (2) adding and then reacting radioactive substance-labeled, enzyme-labeled or affinity substance-labeled secondary antibody, (3) in case of radioactive substance-labeled antibody, measuring the emitting bioluminescence, or coloring signal by scintillation, or in case of enzyme-labeled antibody, measuring the emitting bioluminescence, or coloring signal by adding or reacting chemical luminescent substrate, or chemical coloring substrate. Each step may have a washing step arbitrarily.

A diagnosis of anti-cardiac troponin I autoantibody-related diseases may be carried out by measuring the amount of the antibody in collected blood, serum, plasma, urine or tissue of the patient in the above method.

A diagnostic reagent of anti-cardiac troponin I autoantibody-related diseases may be consist of at least (1) a block for measuring which is electrostatically, chemically, or biochemically bound by human cardiac troponin I or partial protein thereof, (2) a dilution buffer for blood, serum, plasma, urine, or tissue extract of the patient, (3) radioactive substance-labeled, enzyme-labeled, or affinity substance-labeled secondary antibody, and (4) affinity substance-labeled enzyme in case of affinity substance-labeled secondary antibody, (5) in case of radioactive substance-labeled antibody, scintillation; or in case of affinity substance-labeled or enzyme-labeled secondary antibody, chemical luminescent substrate, or chemical coloring substrate.

INDUSTRIAL APPLICABILITY

Application to Pharmaceuticals:

The substance of the present invention that inhibits the interaction between anti-cardiac troponin I antibody and cardiac troponin I, the effect of anti-cardiac troponin I antibody to the target tissue, or the production of anti-cardiac troponin I autoantibody is useful for the therapy of the anti-cardiac troponin I-derived disease when it is administrated in pharmaceutically acceptable way. Cardiac disease includes cardiomyopathy (dilated cardiomyopathy, familial hypertrophic cardiomyopathy, hypertrophic cardiomyopathy, primary cardiomyopathy, idiopathic cardiomyopathy, secondary cardiomyopathy, congestive cardiomyopathy, restrictive cardiomyopathy), myocardial infarction, post-myocardial infarction syndrome, post-pericardial incision syndrome, pericarditis (pericarditis due to collagen disease, rheumatic pericarditis, idiopathic pericarditis), endocarditis, myocarditis and the like.

The substance of the present invention may be used as a solid preparation or liquid preparation for internal use which is formulated to mix with pharmacologically acceptable solvent in case of oral administration, or as a injection, external medicine, suppository and the like which is formulated to mix with pharmacologically acceptable solvent in case of parenteral administration.

Examples of the solid preparations for internal use for oral administration include tablets, pills, capsules, powders, granules and the like. The capsules include hard capsules and soft capsules.

Such a solid preparation for internal use is prepared by a formulation method commonly employed by using one or more than two active substances either as the very thing or as a mixture with an excipient (lactose, mannitol, glucose, microcrystalline cellulose, starch, etc.), a binder (hydroxypropylcellulose, polyvinylpyrrolidone, magnesium metasilicate aluminate, etc.), a disintegrating agent (calcium cellulose glycolate, etc.), a lubricant (magnesium stearate, etc.), a stabilizer and a dissolution aid (glutamic acid, aspartic acid, etc.). If necessary, it may be coated with a coating agent (sucrose, gelatin, hydroxypropylcellulose, hydroxypropylmethylcellulose phthalate, etc.). It may be coated with two or more layers. Moreover, capsules made of an absorbable substance such as gelatin are involved in the scope thereof.

The liquid preparations for internal use for oral administration include pharmaceutically acceptable aqueous solutions, suspensions, emulsions, syrups, elixirs and the like. Such a liquid preparation is prepared by dissolving, suspending or emulsifying one or more active substances in a diluent commonly employed (purified water, ethanol or a mixture thereof, etc.). Such liquid forms may also further comprise some additives such as humectants, suspending agents, emulsifying agents, sweetening agents, flavoring agents, aroma, preservatives, buffers and the like.

The injections for parenteral administration include solutions, suspensions, emulsions and solid injections to be dissolved or suspended before use. Such an injection is used by dissolving, suspending or emulsifying one or more active substances in a solvent. The solvent includes, for example, distilled water for injection, physiological saline, vegetable oils, alcohols such as propylene glycol, polyethylene glycol and ethanol, and mixtures thereof. The injection may further contain a stabilizer, a dissolution aid (glutamic acid, aspartic acid, Polysorbate 80 (registered trademark), etc.), a suspending agent, an emulsifier, a soothing agent, a buffer, a preservative, and the like. Such an injection may be produced by sterilizing at the final step or employing an aseptic process. Alternatively, it is also possible that an aseptic solid product such as a freeze-dried product is produced and sterilized or dissolved in aseptic distilled water for injection or another solvent before use.

Other formations for parenteral administration include liquid preparation for external use, ointment, swab preparation, inhalant, spray, suppository and pessary for intravaginal administration which is prescribed in a general method.

Atomized agents, inhalations and sprays may contain, in addition to a diluent commonly employed, a stabilizer such as sodium hydrogen sulfite, a buffering agent for imparting isotonicity, for example, an isotonic agent such as sodium chloride, sodium citrate or citric acid. Methods for producing a spray are described in detail in, for example, U.S. Pat. No. 2,868,691 and U.S. Pat. No. 3,095,355.

A pharmaceutical component for therapy of the present invention is usually administrated locally or systemically via an oral or parenteral route.

The dose of these compounds depends on the age, weight and symptom of the patient, the remedial value, the administration method, the treatment time, etc. In practice, however, these compounds are administered orally once or several times per day each in an amount of 0.1 mg to 100 mg per adult, parenterally once or several times per day each in an amount of 0.01 mg to 30 mg, per adult or continuously administered into vein for 1 hour to 24 hours per day.

It goes without saying that the dose of these compounds may be less than the aforementioned value or may need to exceed the aforementioned range because the dose varies under various conditions as mentioned above.

BEST MODE FOR CARRYING OUT THE INVENTION

The following reference examples and examples illustrate, but do not limit the present invention.

EXAMPLE 1

Purification and Identification of the 30-kDa Autoantigen:

(a) Solubilization and Purification of 30-kDa Band

Figure 1:
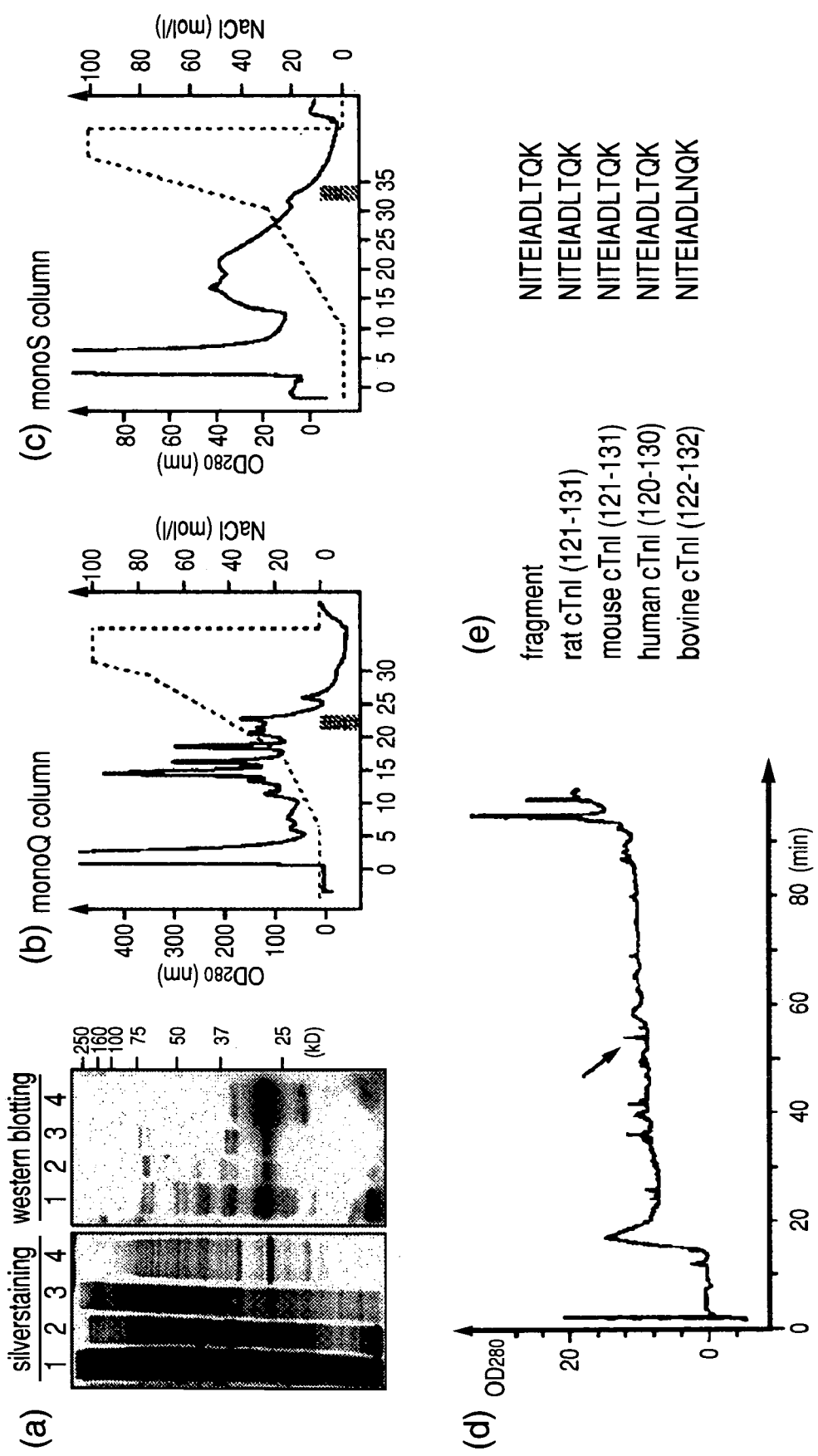
FIG. 1 indicates the result of purification and identification of the 30-kDa autoantigen; (a) silver-staining (left) and western blotting with PD-1-deficient mouse serum (right), (b) anion-exchange column chromatography, (c) cation-exchange column chromatography, (d) reverse phase HPLC column chromatography, and (e) comparison of the amino acid sequences of cardiac troponin I with purified band.

The 30-kDa antigen was purified from extract of rat hearts. Rat hearts were homogenized in a detergent-free buffer (0.25 M sucrose with complete protease inhibitor cocktail (Roche)), dialyzed against Bis-Tris, buffer (20 mM Bis-Tris, 50 mM NaCl; pH 6.8) and fractionated by a mono-Q column (Amersham Biosciences) with the NaCl gradient. Each fraction was detected by western blotting with sera of PD-1-deficient mice. In FIG. 1 (a), detergent-containing (lane 1) and detergent-free (lane 2) rat heart extracts, fraction 22 of Q sepharose column (lane 3) and fraction 33 of S sepharose column (lane 4) were silver-stained (left) and western blotted (right) with PD-1-deficient mouse serum.

(b) Anion-Exchange Column Chromatography

Rat heart extracts were fractionated by a mono-Q column (Amersham Biosiences) with the NaCl gradient and each fraction was detected by western blotting using PD-1-deficient mouse sera. Antigen-containing fractions (fraction 21 and 22) were indicated by shade in FIG. 1 (b).

(c) Cation-Exchange Column Chromatography

Fractions 21 and 22 of the mono-Q sepharose chromatography were dialyzed against MES buffer (50 mM MES, 50 mM NaCl; pH 5.5) and fractionated by a mono-Q column (Amersham Biosciences). Antigen-containing fractions (fraction 33 and 34) were indicated by shadow in FIG. 1 (c).

(d) Reverse Phase HPLC

Positive fractions were separated with SDS-PAGE. A band approximately 30 kDa in size was excised, in-gel-digested with trypsin and separated by reverse phase HPLC (FIG. 1 (d)).

(e) Comparison of the Amino Acid Sequences of Cardiac Troponin I with that of Purified Band The amino acid sequence of the peptide that was indicated by an arrow in Figure (d) was identified and compared with that of rat, mouse, human and caw cardiac troponin I. The obtained sequence was same as that of cardiac troponin I (cTnI) (FIG. 1 (e)).

EXAMPLE 2

Generation of a Monoclonal Antibody Against Cardiac Troponin I:

Complementary DNA of mouse cardiac troponin I was cloned from mouse cardiac mRNA using reverse transcriptase and PCR. A GST-fusion recombinant protein containing cardiac troponin I was made. Mouse cardiac troponin I protein was obtained by subsequent PreScission protease cleavage (Amersham Pharmacia) of the fusion protein. Immunization of PD-1-deficient mice with this recombinant cardiac troponin I (>95% pure as judged by SDS-PAGE) allowed us to establish monoclonal antibody against mouse cardiac troponin I (the antibody produced by hybridoma designated cTnI-1-4A: it was deposited Apr. 2, 2003 at the International Patent Organism Depositary of National Institute of Advanced Industrial Science and Technology (Tsukuba Central 6, 1-1-1 Higashi, Tsukuba, Ibaraki, Japan; deposit number: FERM P-19287)) and transfer of jurisdiction to international deposit Mar. 5, 2004 (international deposit number: FERM BP-08653)). The monoclonal antibody was detected a 30-kDa band by western blotting of the heart extracts. The size of the band was identical to that recognized by PD-1-deficient mouse serum and commercial goat polyclonal antibody to mouse cardiac troponin I (Santa Cruz).

EXAMPLE 3

Immunological Characterization of Cardiac Troponin I:

(a) Immunoprecipitation of Cardiac Troponin I from Heart Extract

Crude heart extracts were immunoprecipitated by goat polyclonal antibody to cardiac troponin I (Santa Cruz). Supernatant (sup) and precipitate (ppt) were obtained. These were checked for the presence of the 30-kDa antibody by western blotting using PD-1-deficient mouse serum. The result was indicated in FIG. 2 (a) (in the figure, crude means crude heart extract, and sup means supernatant, and ppt means precipitation.). The 30-kDa antigen was detected in the precipitate fraction by western blotting using anti-cardiac troponin I monoclonal antibody. The size of the band was same as that identified by PD-1-deficient mouse serum and goat polyclonal antibody to mouse cardiac troponin I (Santa Cruz).

(b) Competition with Recombinant Cardiac Troponin I

PD-1-deficient mouse serum (mouse #101, #104 and #117) was used for western blotting of normal mouse heart extract. For the competition assay, recombinant cardiac troponin I was added to immune blot solution at 1, 10, and 100 µg/ml. The 30-kDa antigen recognized by PD-1-deficient mouse serum was depleted by immunoprecipitation with antibodies to anti-myocardial troponin I and was recoverable from the pellet fraction (FIG. 2 (b)).

Figure 2:
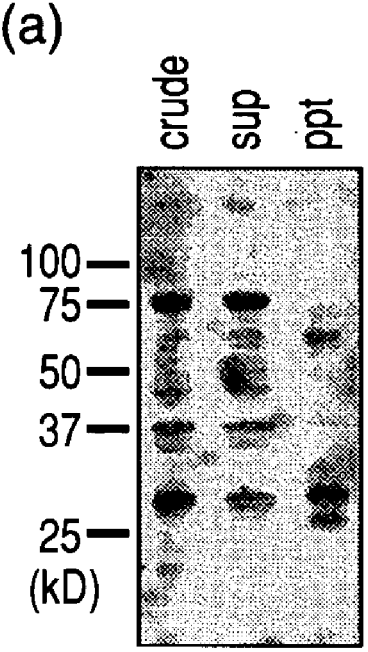
FIG. 2 indicates immunological character of cardiac troponin I in example 3; (a) immunoprecipitation of cardiac troponin I from heart extract, (b) competition with recombinant cardiac troponin I, and (c) immunostaining of normal cardiac slice.
Figure 2:
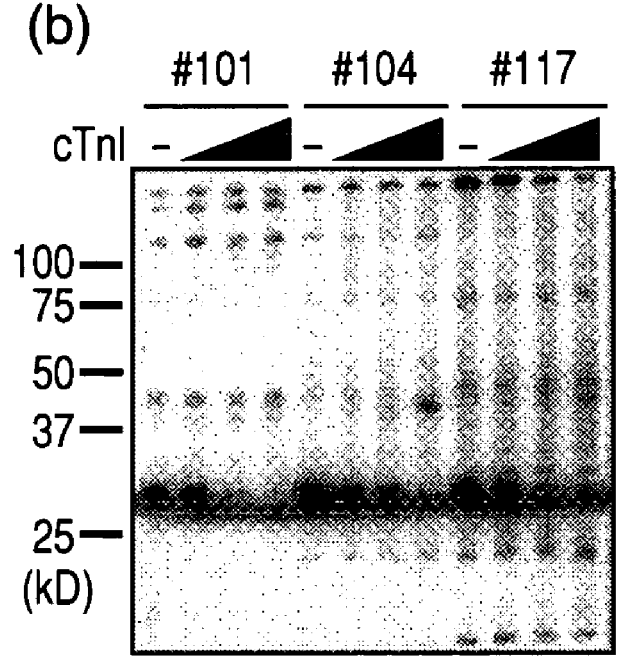
Figure 2:
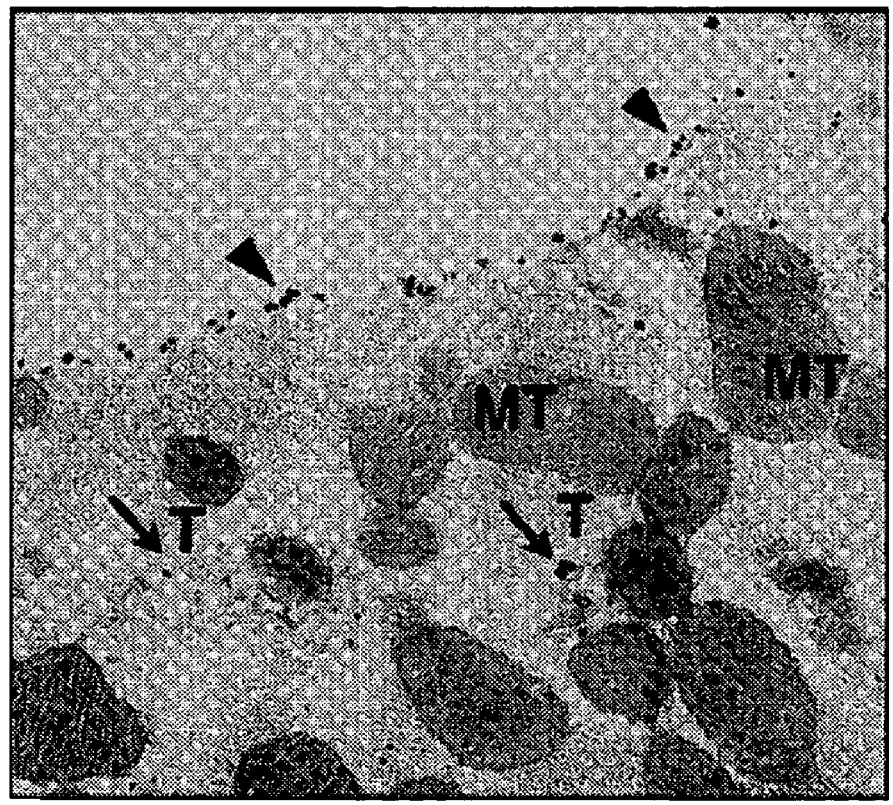

In addition, the intensity of the band recognized by PD-1-deficient mouse serum was weakened in a dose-dependent manner by the addition of recombinant cardiac troponin I, whereas the minor bands were unaffected (FIG. 2 (b)). Thus, the band was confirmed to consist solely of cardiac troponin I.

(c) Immunostaining of Normal Heart Section

The subcellular localization of cardiac troponin I was analyzed by immunoelectron microscopy. The image of normal heart section stained with the 30-kDa autoimmune antibody was shown in FIG. 2 (c). Anti-cardiac troponin I monoclonal antibody stained the surface of cardiomyocytes of normal heart. Arrows indicate signals on the surface of T-tubes, arrowheads indicate signals on the surface of cytomembrane, MT means mitochondria and T means T-tubule. These signals are detected on the outer surface of T-tubules, where L type $Ca^{2+}$ channels are condensed and bound to ryanodine receptor in sarcoplasmic reticulum.

EXAMPLE 4

Hemodynamics of Mice Treated with Anti-Cardiac Troponin I Antibody:

To examine the left-ventricular pressure-to-volume relationships in anti-cardiac troponin I antibody administrated wild type mice, the ventricular function was evaluated by cardiac catheterization. Four-week-old female BALB/c mice were intraperitoneally injected with 600 µg of monoclonal antibodies or 600 µg of control mouse IgG on days 0, 7, 21, 35, 49, 63 and 77 and analyzed on day 82.

Figure 3:
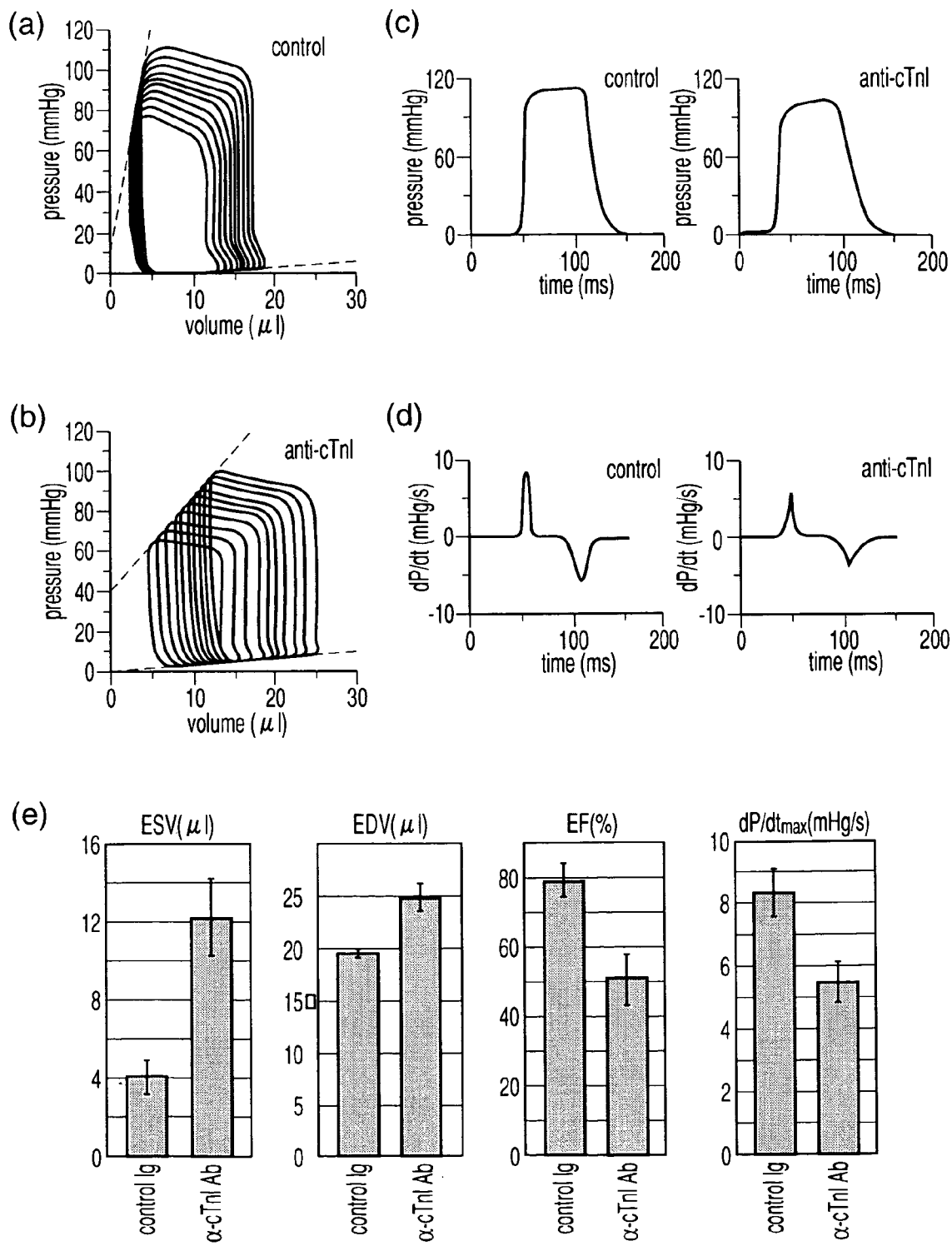
FIG. 3 indicates hemodynamic parameters of mice treated with anti-cardiac troponin I antibody in example 4; (a) the graph of the pressure-to-volume relationship of control IgG administrated mice, (b) the graph of the pressure-to-volume relationship of anti-cardiac troponin I administrated mice (dotted line indicates end-systolic and end-diastolic pressure-to-volume relationship), (c) left-ventricular pressure curve of control IgG treated mice (left) and of anti-cardiac troponin I antibody treated mice (right), (d) the gradient of induction period of systolic pressure change per unit time in control Ig treated mice (left) and in anti-cardiac troponin I antibody treated mice (right), (e) comparison between control IgG treated mice and anti-cardiac troponin I antibody treated mice in ESV (end-systolic volume), EDV (end-diastolic volume), EF (ejection fraction) and maximum pressure driving rate ($dP/dt_{max}$).

FIG. 3 showed the pressure-to-volume relationship in control IgG (FIG. 3(a)) or anti-cardiac troponin I administrated mice (FIG. 3(b)); dotted lines indicate end-systolic and end-diastolic pressure-to-volume relationship), left-ventricular pressure treated with control IgG (FIG. 3(c), left) or cardiac troponin I-specific antibodies (FIG. 3(c), right), the gradient of pressure change per unit time (FIG. 3 (d)) in control IgG treated mice (left) and anti-cardiac troponin I antibodies treated mice (right), and comparison of ESV (end-systolic volume), EDV (end-diastolic volume), EF (ejection fraction) and pressure driving rate (FIG. 3 (e); each value shown represents mean±s.e.m.).

Twelve weeks after the initiation of treatments, the left ventricles of the antibody-treated mice had increased end-systolic volume (ESV) and end-diastolic volume (EDV) (+198%, and +29%, respectively), which resulted in the reduction of ejection fraction from 79.3% in controls to 50.8% (FIGS. 3 (a), (b), and (e)). Systolic function was markedly depressed, as reflected by the decreases in pressure development (dP/dt$_{max}$; −35%), the prolongation of the monoexpoential time constant of relaxation (t; 10.1 to 11.7 ms) (FIG. 3 (b), (d), and FIG. 5). Increases in end-diastolic pressure and right atrium pressure (average right atrium pressure) are representative of the heart failure (FIG. 5). These hemodynamic data indicate that administration of antibody to cardiac troponin I caused increases in ESV and EDV of the left ventricle by weakening systolic function.

EXAMPLE 5

Electrophysiological Analyses in Cardiomyocytes Derived from Dilated Hearts of PD-1-Deficient Mice and Effect of Anti-Cardiac Troponin I Antibody on Normal Cardiomyocytes:

The electrophysiological changes in cardiomyocytes of dilated heart of PD-1-deficient mice were analyzed in order to investigate the in vitro effects of anti-cardiac troponin I antibodies on isolated cardiomyocytes. The method of isolation is as follows. Under anesthesia, mice were intubated intratracheally and ventilated. A cannula was inserted into the ascending part of aorta, and then only heart was taken out and suspended by a cannula. Collagenase was injected via a cannula and refluxed the entire heart through coronary artery for 30 minutes. After refluxing collagenase-free solution for several minutes, the heart was put into the beaker and divided gently by tweezers to isolate cardiomyocytes.

Cardiomyocytes were isolated from wild type mice and dilated cardiomyopathy and each single myocytes were investigated by patch clamp. By replacing extracellular potassium ion by cesium ion, only calcium current was measured.

Figure 4:
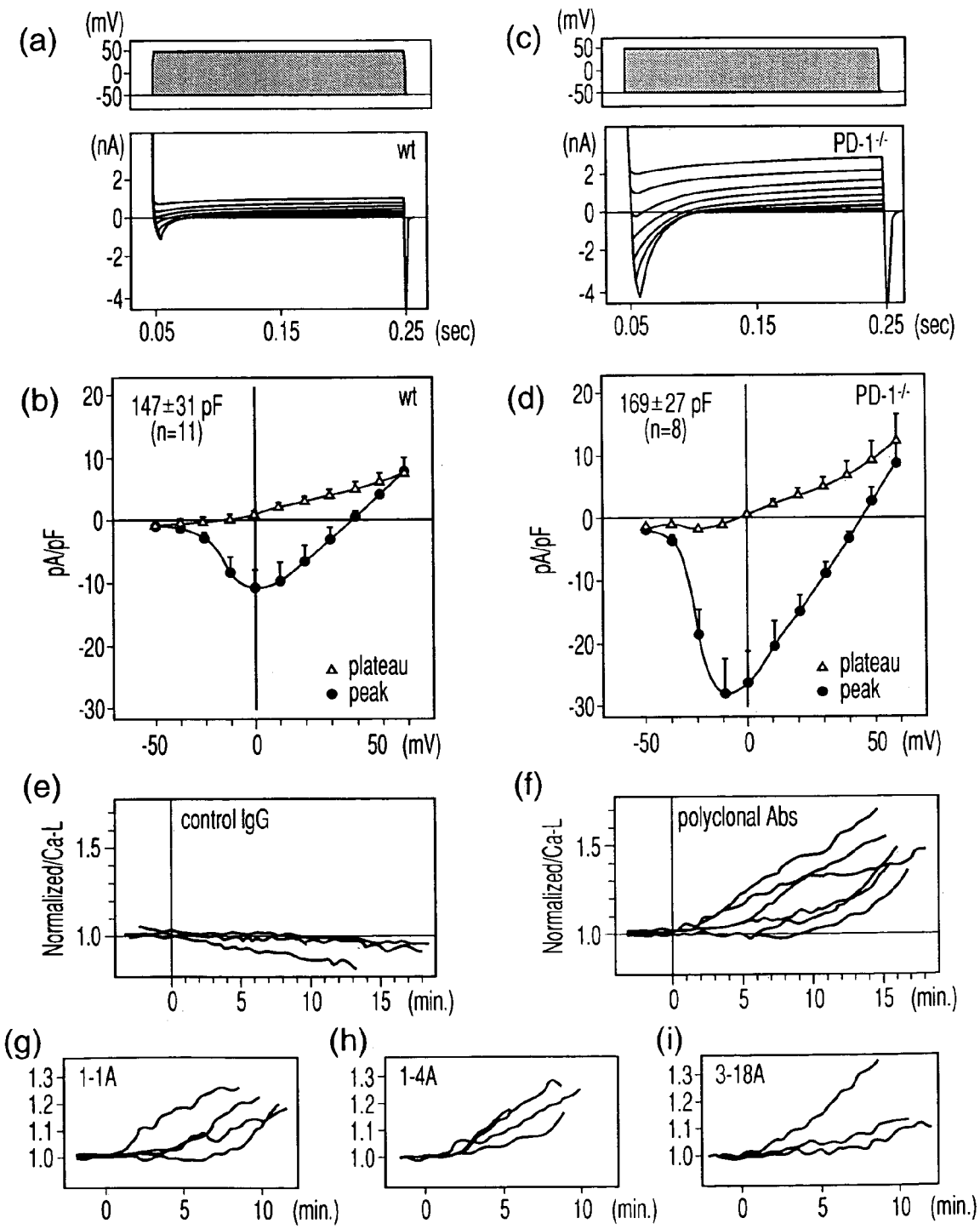
FIG. 4 indicates electrophysiological analysis using cardiomyocytes derived from dilated hearts of PD-1-deficient mice and effect of anti-cardiac troponin I antibody on normal cardiomyocytes; depolarized $Ca^{2+}$ current (lower panel) evoked by a test pulse (upper panel) in (a) wild type (wt) mice and in (c) PD-1-deficient mice; voltage-current relationships of (b) wt mice and of (d) PD-1-deficient mice; (e)-(i) the effect of antibodies against cardiac troponin I on the $Ca^{2+}$ current of normal ventricular cardiomyocytes FIG. 5 indicates data of improvement in hemodynamics of anti-cardiac troponin I antibody treated mice.

Voltage-dependent $Ca^{2+}$ current (lower panel) evoked by a test pulse (upper panel) in cardiomyocytes from wild type (wt) mice (FIG. 4(a)) and PD-1-deficient mice (FIG. 4 (c)) was plotted and voltage-current relationships were shown for wt mice (FIG. 4 (b)) and PD-1-deficient mice (FIG. 4 (d)) ($Ca^{2+}$ current was normalized based on each membrane capacity and plotted as average±S.E.; ● indicates peak value (peak) and Δ indicates plateau value of $Ca^{2+}$ current (plateau).). FIG. 4 (e)-(i) showed the effects of antibodies against cardiac troponin I on the $Ca^{2+}$ current of normal ventricular cardiomyocytes. Normal ventricular cardiomyocytes were microperfused with (e) control goat IgG, (f) polyclonal antibodies against cardiac troponin I, and monoclonal antibodies against cardiac troponin I (1-1A, 1-4A, or 3-18A, (g)-(i)) and monitored for the inward $Ca^{2+}$ current, evoked by a depolarizing pulse to ±0 mV, every 6 seconds. Each value is presented as ratio against the initial magnitude of the $Ca^{2+}$ current ((e)-(i)).

The maximal voltage-dependent $Ca^{2+}$ current was increased about threefold in cardiomyocytes of dilated hearts (FIG. 4 (a) and (c)). The membrane capacitance of cardiomyocytes didn't change significantly (147±31 pF and 169±27 pF in cardiomyocytes from wt and PD-1 deficient mice, respectively). The variance in the $Ca^{2+}$ current didn't change by normalizing the value of the $Ca^{2+}$ current to membrane capacitance (pA/pF) (FIG. 4 (b), (d)). Therefore, the augmentation of the $Ca^{2+}$ current is likely to be attributable to changes in the L-type $Ca^{2+}$ channel itself.

In the analysis of the effect of antibodies to cardiac troponin I on the $Ca^{2+}$ current of wild-type cardiomyocytes by pouring antibodies to cardiac troponin I from a thin tube, the $Ca^{2+}$ current evoked by the depolarizing pulse to ±0 mV was plotted every 6 seconds and expressed as a ratio against the initial value, because the depolarizing pulse to ±0 mV gave a maximal $Ca^{2+}$ current for the wild-type cardiomyocytes (FIG. 4(b)). Addition of the commercial polyclonal antibody and the three monoclonal antibodies (FIG. 4(g)-(i)) to cardiac troponin I augmented the $Ca^{2+}$ current of ventricular and atrial cardiomyocytes by as much as 1.5-fold (FIG. 4). Control goat IgG or mouse IgG did not affect the $Ca^{2+}$ current over the course of 15 min (FIG. 4). Cardiac troponin I expressed on the surface of cardiomyocytes may be involved, in an unknown capacity, in regulating the magnitude of the $Ca^{2+}$ current. Taken together, these data imply that antibodies to cardiac troponin I induce DCM in PD-1-deficient mice by chronically enhancing the $Ca^{2+}$ current in cardiomyocytes.

The invention claimed is:

1. A diagnosis method of dilated cardiomyopathy, which comprises measuring an amount of anti-cardiac troponin I autoantibody and determining the existence of said antibody to thereby diagnose dilated cardiomyopathy.

2. A method for treating dilated cardiomyopathy, which comprises removing anti-cardiac troponin I autoantibody from a patient's blood.

* * * * *